(12) United States Patent
Botbol et al.

(10) Patent No.: US 7,033,323 B2
(45) Date of Patent: Apr. 25, 2006

(54) METHOD AND SYSTEM FOR ANALYZING RESPIRATORY TRACT AIR FLOW

(75) Inventors: Meir Botbol, Pardes Hana (IL); Igal Kushnir, Pardes Hana (IL)

(73) Assignee: Deepbreeze Ltd., Akiva (IL)

( * ) Notice: Subject to any disclaimer, the term of this patent is extended or adjusted under 35 U.S.C. 154(b) by 0 days.

(21) Appl. No.: 10/771,139

(22) Filed: Feb. 4, 2004

(65) Prior Publication Data

US 2005/0182337 A1   Aug. 18, 2005

(51) Int. Cl.
*A61B 5/08* (2006.01)

(52) U.S. Cl. .................... 600/538; 600/529

(58) Field of Classification Search .................
73/861.18–861.31; 600/529–543, 437, 438
See application file for complete search history.

(56) References Cited

U.S. PATENT DOCUMENTS 6,139,505 A   10/2000   Murphy
6,168,568 B1*  1/2001   Gavriely ................. 600/529
6,241,683 B1   6/2001   Macklem et al.
6,443,907 B1*  9/2002   Mansy et al. ............ 600/529
6,887,208 B1*  5/2005   Kushnir et al. .......... 600/529
2003/0139679 A1  7/2003   Kushnir et al.

FOREIGN PATENT DOCUMENTS

GB   2 129 991 A   5/1984

* cited by examiner

*Primary Examiner*—Robert L. Nasser
*Assistant Examiner*—Patricia Mallari
(74) *Attorney, Agent, or Firm*—Nath & Associates PLLC; Gregory B. Kang; Teresa M. Arroyo

(57) ABSTRACT

A method for determining airflow in a portion of a respiratory tract comprising determining a total acoustic energy in a region of a body surface overlying the portion of the respiratory tract. The airflow may be integrated over a time interval in order to determine an air volume that has flowed in the portion of the respiratory tract during the time interval. A graph of the flow rate as a function of the volume may be displayed and analyzed as in spirometry. The invention also provides a system for carrying out the method.

10 Claims, 2 Drawing Sheets

US 7,033,323 B2

METHOD AND SYSTEM FOR ANALYZING RESPIRATORY TRACT AIR FLOW

FIELD OF THE INVENTION

This invention relates to medical devices and methods and more specifically, to such devices and methods for analyzing respiratory tract function.

BACKGROUND OF THE INVENTION

Spirometry is a common test of respiratory function that involves measuring the total volume of air inhaled into the lungs over a respiratory cycle. A spirometry test is usually carried out by having a subject inhale air through a tube connected to an air flow meter that measures the total volume of air inhaled during the inspiration phase of the respiratory cycle. At the termination of the inspiration phase the subject exhales through the tube. A curve is generated showing the air flow as a function of time. The curve is analyzed to obtain one or more respiratory parameters of the subject that are used to assess intrathorax airways obstruction. For example, the so-called "*forced expiratory volume in one second*" ($FEV_1$) is obtained in a test performed during a maximum effort force expiratory vital capacity maneuver started from total lung capacity. $FEV_1$ is a well characterized test of respiratory function and provides useful information in diseased and normal states. In chronic obstructive pulmonary disease, the level of $FEV_1$ is used to grade the severity of the obstruction.

It is known to attach a plurality of microphones to a subject's chest or back in order to record respiratory tract sounds at a plurality of locations on the body surface. U.S. patent application Ser. No. 10/338,742 published on Jan. 9, 2003, as U.S. Patent Application Publication No. 2003-0139679, and now U.S. Pat. No. 6,887,208 discloses a method for analyzing respiratory tract sounds detected by a plurality of microphones affixed to a subject's back or chest. The recorded sound signals are processed to determine an average acoustical energy $\bar{P}(x,t1,t2)$ at a plurality of locations x on the body surface over a time interval from $t_1$ to $t_2$.

SUMMARY OF THE INVENTION

The present invention is based on the finding that the average acoustic energy over a region of an individual's back or chest or during a time interval from $t_1$ to $t_2$, can be correlated with the air flow in the portion of the respiratory tract underlying the region during that time interval. Thus, in its first aspect the invention provides a method for calculating an air flow in at least a portion of an individual's respiratory tract. In accordance with this aspect of the invention, a plurality of microphones is fixed onto a subject's back or chest over the portion of the respiratory tract, and respiratory tract sounds are recorded from the region over a time interval from $t_0$ to $t_1$. An average acoustical energy during the subinterval is determined at a plurality of locations x in the region. The total average acoustical energy, summed over the locations x is then correlated with the airflow in the portion of the respiratory tract. In a presently preferred embodiment, an airflow is calculated that is equal to the logarithm of the total acoustic energy. The process may then be repeated during the expiratory phase of the respiratory cycle.

The airflow during each subinterval obtained by the method of the invention, may be displayed in the form of a graph of the airflow as a function of time over a respiratory cycle.

The airflow in the lungs as a function of time during the inspiratory phase obtained in accordance with the invention may be integrated from a time $t_0$ to a time t to produce a total volume of air that has flowed into the airways from time $t_0$ to t. The airflow at a time t may be plotted as a function of the total volume of air that has flowed into the airways from $t_0$ to time t, to produce a spirometry curve for inspiration. The process may then be repeated for the expiratory phase of the respiratory cycle. Thus, in its first aspect, the invention provides a method for determining airflow in a portion of a respiratory tract comprising determining a total acoustic energy in a region of a body surface overlying the portion of the respiratory tract.

In its second aspect, the invention provides a system for determining airflow in a portion of a respiratory tract comprising a processor configured to determine a total acoustic energy in a region of a body surface overlying the portion of the respiratory tract.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
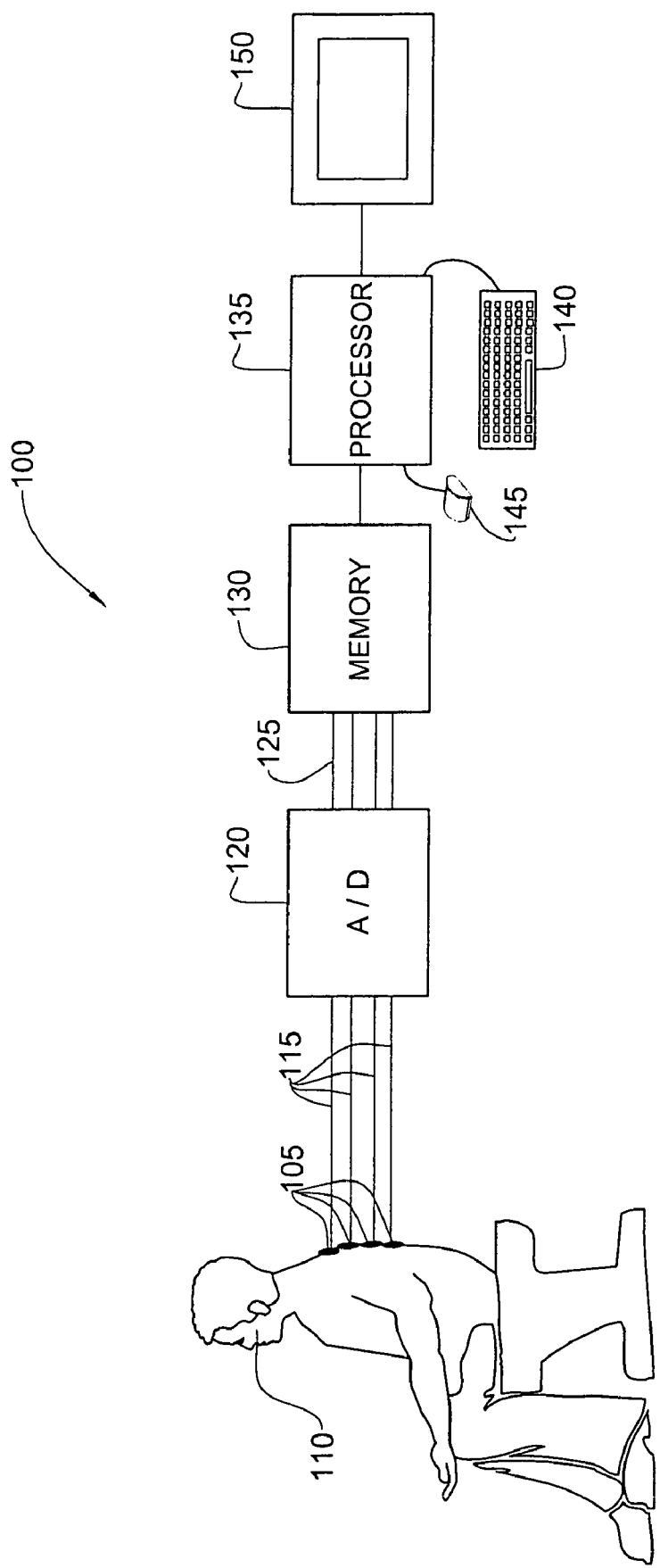
FIG. 1 shows a system for analyzing respiratory tract airflow in accordance with one embodiment of the invention.

FIG. 1 shows a system generally indicated by 100 for analyzing respiratory tract airflow in accordance with one embodiment of the invention. A plurality of N sound transducers 105, of which four are shown, are applied to a planar region of the chest or back skin of individual 110. The transducers 105 may be applied to the subject by any means known in the art, for example using an adhesive, suction, or fastening straps. Each transducer 105 produces an analog voltage signal 115 indicative of pressure waves arriving to the transducer. The system 100 is used to obtain acoustic signals 115 over a time interval from $t_0$ to $t_m$. The analog signals 115 are digitized by a multichannel analog to digital converter 120. The digital data signals $P(x_i,t)$ 125, represent the pressure wave at the location $x_i$ of the ith transducer (i=1 to N) at time t. The data signals 125 are input to a memory 130. Data input to the memory 130 are accessed by a processor 135 configured to process the data signals 125. The signals 125 may be denoised by filtering components having frequencies outside of the range of respiratory sounds, for example, vibrations due to movement of the individual. Each signal 125 may also be subject to band pass filtering so that only components in the signal within a range of interest are analyzed.

An input device such as a computer keyboard 140 or mouse 145 is used to input relevant information relating to the examination such as personal details of the individual 110. The input device 140 may also be used to input a subdivision of the time interval $t_0$ to $t_m$ into subintervals $t_0$, $t_1$, $t_2$, ... $t_m$. Alternatively, the times $t_2$, ... $t_{m-1}$ may be determined automatically by the processor 135. The processor 135 determines an average acoustic energy p̃(x,ti,ti+1) over each subinterval from ti to $t_{i+1}$, i=0 to m−1. at a plurality of locations x in the region R in a calculation involving at least one of the signals $P(x_i,t)$.

The average acoustic energies are stored in the memory 130 and may be displayed on a display device 150 such as a CRT screen for diagnosis by a physician.

The processor is also configured to integrate the functions p̃(x,ti,ti+1) with respect to x $$\sum_x \tilde{P}(x, t_i, t_{i+1})$$

in order to obtain a total flow rate of air in the airways during the interval from $t_i$ to $t_{i+1}$. The processor is also configured to integrate the functions $$\sum_x \tilde{P}(x, t_i, t_{i+1})$$

with respect to time, $$\sum_{t_0}^{t_k} \sum_x \tilde{P}(x, t_i, t_{i+1}),$$

in order to obtained the total volume of air that has flowed in the airways from $t_0$ to $t_k$, for each k from 1 to m.

The processor is also configured to display on the display device a spirometry curve which is a plot of the flow rate $$\sum_x \tilde{P}(x, t_i, t_{i+1})$$

during the interval from $t_i$ to $t_{i+1}$ as a function of the volume $$\sum_{t_0}^{t_k} \sum_x \tilde{P}(x, t_i, t_{i+1})$$

suring the same time interval.

The processor 135 may also perform an automatic differential diagnosis by comparing the spirometry curve to standard spirometry curves functions stored in the memory and known to be indicative of various disorders in the body region.

Figure 2:
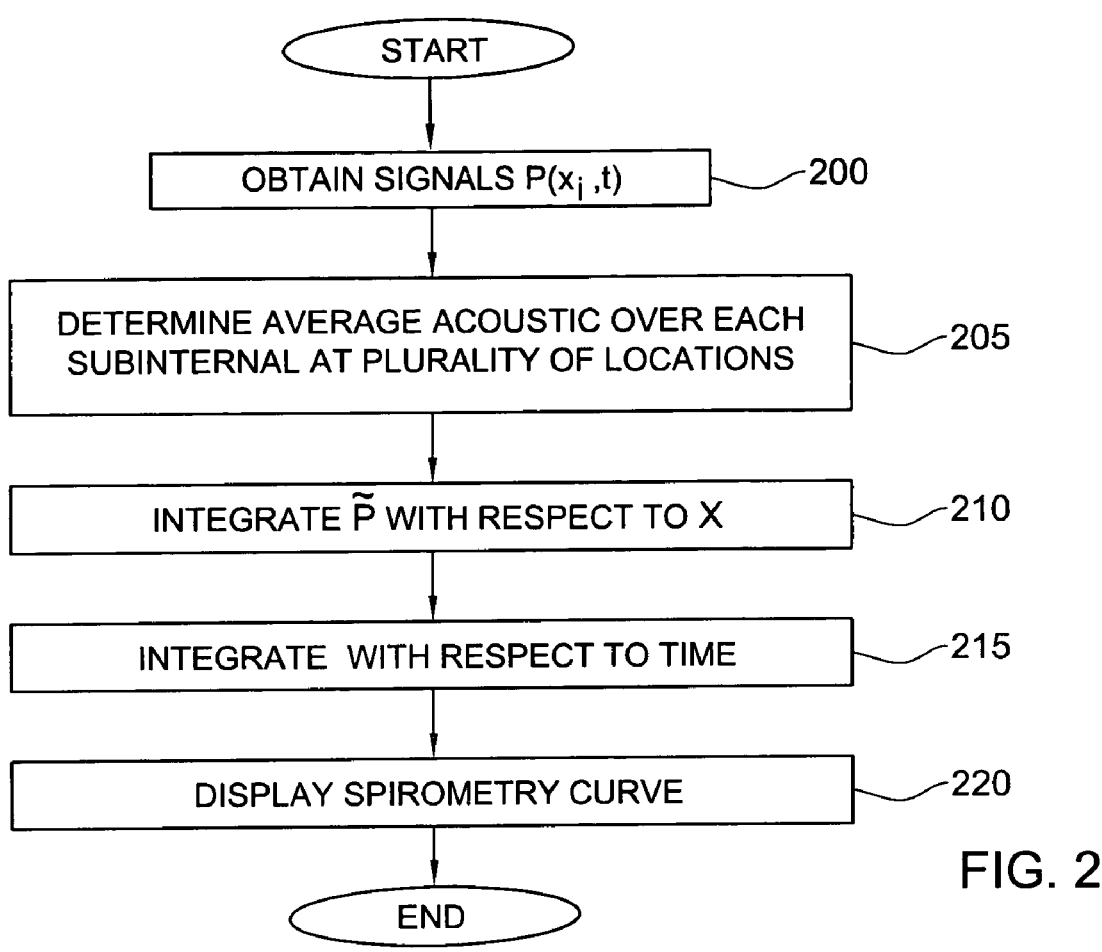
FIG. 2 shows a flow chart diagram for carrying out the method of the invention in accordance with one embodiment of the invention.

FIG. 2 shows a flow chart diagram for carrying out the method of the invention in accordance with one embodiment. In step 200 the signals $P(x_i,t)$ are obtained from N transducers placed at predetermined locations $x_i$ for i from 1 to N in a region R on an individual's chest or back. In step 205 the processor 135 determines an average acoustic energy p̃(x,ti,ti+1) over each subinterval from $t_i$ to $t_{i+1}$, i=0 to m−1 at a plurality of locations $x_i$ in the region R in a calculation involving at least one of the signals $P(x_i,t)$.

In step 210, the processor integrates the functions p̃(x,ti, ti+1) with respect to x, $$\sum_x \tilde{P}(x, t_i, t_{i+1})$$

in order to obtain a total flow rate of air in the airways during the interval from $t_i$ to $t_{i+1}$. In step 215, the processor integrates the functions $$\sum_x \tilde{P}(x, t_i, t_{i+1})$$

with respect to time, $$\sum_{t_0}^{t_k} \sum_x \tilde{P}(x, t_i, t_{i+1}),$$

in order to obtained the total volume of air that has flowed in the airways from $t_0$ to $t_k$, for each k from 1 to m. In step 220, the processor displays on the display device a spirometry curve which is a plot of the flow rate $$\sum_x \tilde{P}(x, t_i, t_{i+1})$$

as a function of the volume $$\sum_{t_0}^{t_k} \sum_x \tilde{P}(x, t_i, t_{i+1}).$$

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

EXAMPLES

A plurality of 20 sound transducers were applied to an individual's back over each lung. Each transducer produced an analog voltage signal indicative of pressure waves arriving to the transducer over a respiratory cycle. The analog signals were digitized by a multichannel analog to digital converter. The digital data signals $P(x_i,t)$, represent the pressure wave at the location $x_i$ of the ith transducer at time t. The data signals were denoised by filtering components having frequencies outside of the range of respiratory sounds.

The respiratory cycle was divided into 0.1 sec subintervals and the subintervals were classified as belonging to either the inspiratory or the expiratory phase of the respiratory cycle. An average acoustic energy was calculated $\bar{p}(x,ti,ti+1)$ over each subinterval $[t_i, t_{i+1}]$ at a plurality of locations x over each lung from the signals $P(x_i,t)$.

Figure 3A:
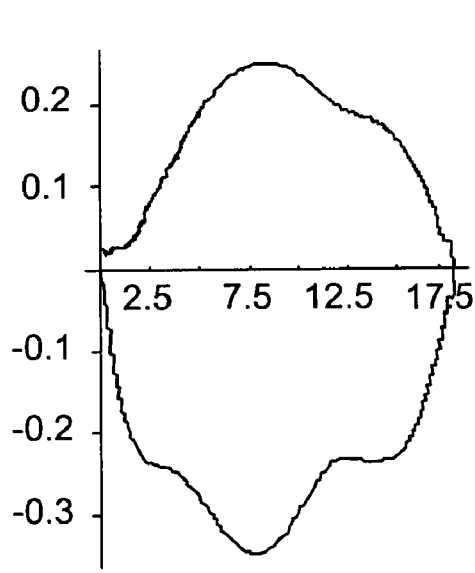
FIG. 3a shows a spirometry curve for both lungs of an individual.
Figure 3B:
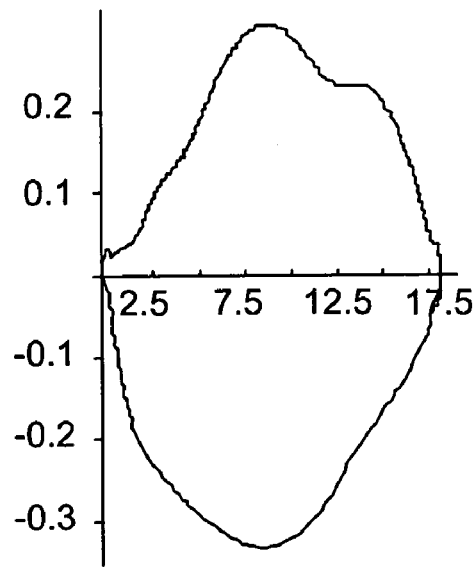
FIG. 3b shows a spirometry curve for the right lung.

For each lung, the functions $\bar{p}(x,ti,ti+1)$ were integrated with respect to x $$\sum_x \bar{P}(x, t_i, t_{i+1})$$

in order to obtain a total airflow in the lung during the interval from $t_i$ to $t_{i+1}$. The integrals $$\sum_x \bar{P}(x, t_i, t_{i+1})$$

were then integrated with respect to time, $$\sum_{t0}^{tk} \sum_x \bar{P}(x, t_i, t_{i+1}),$$

in order to obtain a function that can be correlated with the total volume of air that has flowed into or out of each lung during the inspiratory and the expiratory phase, respectively, from the onset of the phase to a variable time $t_k$. The logarithm of these integrals were calculated and plotted as a function of time during the respiratory cycle in order to obtain a spirometry curve. The results are shown in FIG. 3. FIG. 3a shows a spirometry curve for both lungs. The portion of the curve corresponding to the expiratory phase of the respiratory cycle is plotted above the horizontal axis. The portion of the curve corresponding to the expiratory phase of the respiratory cycle is plotted below the horizontal axis. The volume values in the vertical axis may be correlated by using spirometry data of the individual obtained from a mechanical spirometer. FIG. 3b shows a spirometry curve for the right lung. The volume values in the vertical axis may be correlated by using spirometry data of the individual obtained from a mechanical spirometer on both lungs.

The invention claimed is:

1. A method for determining airflow in a portion of a respiratory tract comprising:
   determining an average acoustic energy in a region of a body surface overlying the portion of the respiratory tract,
   wherein the average acoustic energy is determined in a process comprising:
   (a) obtaining signals P(xi,t) from N transducers placed at predetermined locations $x_i$ for i from 1 to N in the region of the body surface;
   (b) determining an average acoustic energy $\bar{p}(x,ti,ti+1)$ over one or more time intervals ti to $t_{i+1}$, at a plurality of locations x in the region in a calculation involving at least one of the signals $P(x_i,t)$; and
   (c) integrating the functions $\bar{p}(x,ti,ti+1)$ with respect to x, $$\sum_x \bar{P}(x, t_i, t_{i+1})$$

in order to obtain an airflow in the region during each of the time intervals.

2. The method according to claim 1 further comprising calculating a logarithm of an acoustical energy.

3. The method according to claim 1 further comprising integrating the functions $$\sum_x \bar{P}(x, t_i, t_{i+1})$$

with respect to time, $$\sum_{t0}^{t_k} \sum_x \bar{P}(x, t_i, t_{i+1})$$

in order to obtain a total volume of air that has flowed in the region from $t_0$ to $t_k$, for each k from 1 to m.

4. The method according to claim 3 further comprising displaying on a display device a plot of the flow rate $$\sum_x \bar{P}(x, t_i, t_{i+1})$$

as a function of the volume $$\sum_{t0}^{t_k} \sum_x \bar{P}(x, t_i, t_{i+1}).$$

5. The method according to claim 1, wherein the region is a single lung or a lobe of a lung.

6. A system for determining airflow in a portion of a respiratory tract comprising:
   a processor configured to determine an average acoustic energy in a region of a body surface overlying the portion of the respiratory tract,
   wherein the average acoustic energy is determined in a process comprising:
   (a) obtaining signals P(xi,t) from N transducers placed at predetermined locations $x_i$ for i from 1 to N in the region of the body surface;
   (b) determining an average acoustic energy $\bar{p}(x,ti,ti+1)$ over one or more time intervals ti to $t_{i+1}$, at a plurality of locations x in the region in a calculation involving at least one of the signals $P(x_i,t)$ and
   (c) integrating the functions $\bar{p}(x,ti,ti+1)$ with respect to x, $$\sum_x \bar{P}(x, t_i, t_{i+1})$$

in order to obtain an airflow in the region during each of the time intervals.

7. The system according to claim 6, wherein the region is a single lung or a lobe of a lung.

8. The system according to claim 6, wherein the processor is further configured to calculate a logarithm of an acoustical energy.

9. The system according to claim 6 wherein the processor is further configured to integrate the functions $$\sum_x \tilde{P}(x, t_i, t_{i+1})$$

with respect to time, $$\sum_{t_0}^{t_k} \sum_x \tilde{P}(x, t_i, t_{i+1})$$

in order to obtain a total volume of air that has flowed in the region from $t_0$ to $t_k$, for each k from 1 to m.

10. The system according to claim 9 further comprising display device and wherein the processor is further configured to displaying on the display device a plot of the flow rate $$\sum_x \tilde{P}(x, t_i, t_{i+1})$$

as a function of the volume $$\sum_{t_0}^{t_k} \sum_x \tilde{P}(x, t_i, t_{i+1}).$$

* * * * *